(12) United States Patent
Pedrani

(10) Patent No.: US 10,828,268 B2
(45) Date of Patent: Nov. 10, 2020

(54) MODIFIED-RELEASE THERAPEUTIC SYSTEMS FOR ORAL ADMINISTRATION OF CURCUMIN IN THE TREATMENT OF INTESTINAL DISORDERS

(71) Applicant: MOGON PHARMACEUTICALS SAGL, Melide (CH)

(72) Inventor: Massimo Pedrani, Melide (CH)

(73) Assignee: MOGON PHARMACEUTICALS SAGL, Melide (CH)

( * ) Notice: Subject to any disclaimer, the term of this patent is extended or adjusted under 35 U.S.C. 154(b) by 526 days.

(21) Appl. No.: 15/103,086

(22) PCT Filed: Dec. 10, 2014

(86) PCT No.: PCT/IB2014/066764
§ 371 (c)(1),
(2) Date: Jun. 9, 2016

(87) PCT Pub. No.: WO2015/087259
PCT Pub. Date: Jun. 18, 2015

(65) Prior Publication Data
US 2018/0133172 A1    May 17, 2018

(30) Foreign Application Priority Data

Dec. 11, 2013 (IT) .............................. MI2013A2065

(51) Int. Cl.
| | | |
|---|---|---|
| *A61K 31/12* | (2006.01) | |
| *A61K 36/9066* | (2006.01) | |
| *A61K 9/20* | (2006.01) | |
| *A61K 9/28* | (2006.01) | |
| *A61K 45/06* | (2006.01) | |
| *A61P 1/00* | (2006.01) | |

(52) U.S. Cl.
CPC .............. *A61K 31/12* (2013.01); *A61K 9/205* (2013.01); *A61K 9/2031* (2013.01); *A61K 9/2054* (2013.01); *A61K 9/2059* (2013.01); *A61K 9/282* (2013.01); *A61K 9/286* (2013.01); *A61K 9/288* (2013.01); *A61K 9/2846* (2013.01); *A61K 9/2866* (2013.01); *A61K 36/9066* (2013.01); *A61K 45/06* (2013.01); *A61P 1/00* (2018.01)

(58) Field of Classification Search
None
See application file for complete search history.

(56) References Cited

U.S. PATENT DOCUMENTS

| | | |
|---|---|---|
| 7,115,297 B2 | 10/2006 | Stillman |
| 2010/0215779 A1* | 8/2010 | Currie ................ A61K 31/4706 424/725 |

FOREIGN PATENT DOCUMENTS

| | | |
|---|---|---|
| CN | 101780055 A | 7/2010 |
| WO | 2005123042 A1 | 12/2005 |
| WO | 2011002972 A2 | 1/2011 |

OTHER PUBLICATIONS

Search Report of counterpart Russian Application No. 2016122896/15 dated Jun. 14, 2018.
Office Action issued on counterpart Russian Application No. 2016122896/15 dated Jul. 2, 2018.
Gazzaniga A., et al., "Time-controlled oral delivery systems for colon targeting", Expert Opinion on Drug Delivery, Informa Healthcare, GB, vol. 3, No. 5, Jan. 1, 2006, pp. 583-597.
Habibur Rahman, et al., "Influence of Momordica charantia in physical properties and release profile of curcumin formulations", Biosciences Biotechnology Research Asia, Oriental Scientific Publishing Company In. vol. 5, No. 1 Jun. 1, 2008 pp. 377-382.
Search Report and Written Opinion of PCT/IB2014/066764 dated Mar. 24, 2015.
Chinese Office Action issued in counterpart Chinese application dated Jun. 3, 2019.
Habibur Rahman S.M., et al., "Influence of Momordica charantia in physical properties and release profile of curcumin formulations," Biosciences, Biotechnology Research Asia, vol. 5(1), 377-382 (2008).
Letter reporting Chinese Office Action issued in counterpart application.
Translation of Chinese Office Action issued in counterpart Chinese application.
Yu J., et al. "Study on prescription and process of curcum in cobin-specific Tablet", Chinese Archives of Traditional Chinese Medicine, vol. 28, No. 12, (2010), 2565-2567.

* cited by examiner

*Primary Examiner* — Dominic Lazaro
(74) *Attorney, Agent, or Firm* — Silvia Salvadori, P.C.

(57) ABSTRACT

Disclosed are colon-specific delayed-release pharmaceutical compositions comprising: a) a matrix consisting of hydrophilic substances wherein curcumin is dispersed; b) a gastroresistant or acid-resistant pH-independent coating with a lag time of matrix a).

9 Claims, No Drawings

MODIFIED-RELEASE THERAPEUTIC SYSTEMS FOR ORAL ADMINISTRATION OF CURCUMIN IN THE TREATMENT OF INTESTINAL DISORDERS

This application is a U.S. national stage of PCT/IB2014/066764 filed on 10 Dec. 2014, which claims priority to and the benefit of Italian Application No. MI2013A002065 filed on 11 Dec. 2013, the contents of which are incorporated herein by reference in their entireties.

The present invention relates to modified-release compositions containing curcumin incorporated in hydroxypropylmethylcellulose matrices loaded into a gastroresistant monolithic system, able to provide optimum release profiles for the treatment of intestinal disorders.

The compositions according to the invention modulate the activity of curcumin, reducing its frequency of administration and modulating its release in particular sites of the gastrointestinal tract.

The compositions according to the invention are useful in the treatment of intestinal disorders of inflammatory, immunological and/or systemic origin, in particular in the treatment of gastrointestinal disorders, irritable bowel syndrome, Crohn's disease and ulcerating colitis.

PRIOR ART

Curcumin is obtained by extraction with solvent from the dried, ground rhizome of the *Curcuma longa* plant (*Turmeric domestica* Valeton). As the extract must be separated from the flavourings present, it is purified by crystallisation. It is accompanied by small amounts of its demethoxy- and bis-demethoxy-derivatives, ie. derivatives which lack one or both —OCH3 groups.

The product obtained is liposoluble, with a bright greenish-yellow colour.

In order to be suitable for dietary use, the sum of the curcumin and the demethoxylated derivatives thereof must be not less than 90% of the total.

The rhizomes of *Curcuma longa* (turmeric) also contain minor amounts of oils and resins such as sesquiterpenes (ketones and alcohols; alpha-turmerone, beta-turmerone, curlon, zingiberene, ar-turmerone, turmenorol A and turmenorol B.

Human clinical trials demonstrate that curcumin is a poorly bioavailable molecule when taken orally; specifically, curcumin is rapidly conjugated at hepatic and intestinal level to curcumin glucuronide and curcumin sulphate, or reduced to hexahydrocurcumin; these metabolites perform a lower biological activity than curcumin. Pharmacokinetics studies have demonstrated that if curcumin is taken at doses lower than 3.6-4 g/day, curcumin and its metabolites may be undetectable in the plasma. Scientific evidence exists that curcumin, when administered orally, tends to accumulate in the tissues of the digestive apparatus, where it performs its most interesting, proven biological and therapeutic activities.

In view of these properties, a particularly desirable objective is colon-specific release of curcumin starting from the distal ileum with a suitable lag time until the distal part of the small intestine is reached, thus ensuring slow, gradual, constant release of the product throughout the colonic tract.

Curcumin formulations characterised by immediate release are known and already available on the market, but their active ingredient release profile is unsatisfactory, because it does not guarantee homogenous release throughout the colonic tract.

WO 2013/171270 discloses gastroresistant formulations of curcumin combined with absorption promotors (chitosan, black pepper extract, N-acetylcysteine, grapefruit extract). Said formulations are not controlled-release or extended-release formulations.

WO 2008/059522 discloses a reservoir system based on pellets with different gastroresistant coatings. Curcumin is exemplified in a multiparticulate reservoir system which can be coated with various gastroresistant polymers, wherein hydroxypropylmethylcellulose is only used to promote loading of the curcumin on the pellets, not to modify its release, which takes place in less than 15 minutes.

CN 101791298 discloses curcumin tablets coated with zein, pectin and microcrystalline cellulose for release in the colon. It is a "reservoir" formulation which, depending on the quantity of coating, produces substantially pH-independent controlled releases with the aim of reaching the distal part of the ileum/initial part of the colon. The release mechanism is therefore regulated only by the coating and can provide controlled or delayed release, depending on the quantities of zein. The release of the active ingredient in the enteric tract, especially the colon, cannot take place gradually and constantly over time.

DESCRIPTION OF THE INVENTION

It has now been found that an optimum colon-specific slow release of curcumin can be obtained with monolithic pharmaceutical compositions comprising:

a) a core containing hydroxypropylmethylcellulose wherein the curcumin is dispersed;

b) a gastroresistant coating of core a).

The formulations according to the invention, characterised by a core with a monolithic matrix, are able to modulate, control and slow the release of the active ingredient within 8-24 hours. The gastroresistant coating of the core prevents release in vitro for at least 2 hours under conditions of pH<1.2-5.5.

The gastroresistant coating typically consists of cellulose derivatives, cellulose phthalates, succinates, methacrylic or polymethacrylic acid polymers, shellac or alginates, preferably of shellac and hydroxypropylmethylcellulose, or ethylcellulose with alginic acid, or polymethacrylates (pH-dependent), ethylcellulose or hydroxypropylmethylcellulose (pH-independent/lag time). A mixture of shellac and hydroxypropylmethylcellulose is particularly preferred.

The matrix core is coated with a quantity of polymer/resin sufficient to guarantee that it remains intact in gastric and enteric juice for at least 2-4 hours before the release of the active ingredient from the core (lag time). To reduce the impact of the variability of gastric voiding times, the formulations can include a further gastroresistant coating (pH-dependent) external to the matrix core (pH-independent) and to the cellulose film-coating (pH-independent), to further delay contact between the biological fluids and the modified-release core (extended release).

In this way the system prevents early release during the stomach-jejunum transit time, and slow release up to 24 hours is obtained to ensure homogenous distribution of the medicament in the ascending, transverse and descending tracts of the large intestine.

The compositions according to the invention therefore differ from the usual delayed-release forms (gastroresistant and/or with lag time), which can reach the distal part of the ileum and/or the initial part of the colon, but then rapidly release the active constituent without being distributed evenly in the colonic tract.

The use of hydroxypropylmethylcellulose with different rheological characteristics (viscosity/swelling properties) of the matrix core allows the release to be modulated in a gradual, programmed way for between 8 and 24 hours. The hydroxypropylmethylcellulose usable according to the invention has an apparent viscosity measured at 20° C. in 2% aqueous solution ranging between 3 and 200,000 mPs, preferably between 30 and 150,000, and more preferably between 50 and 100,000. A single type of hydroxypropylmethylcellulose, or a mixture of at least two types of hydroxypropylmethylcellulose with different viscosities, can be used. Hydroxypropylmethylcellulose is available on the market from Dow Chemical under the Methocel brands, or from Ashland under the Benecel brands. Preferred examples of hydroxypropylmethylcellulose are those having the same characteristics as the commercial products Methocel K100lv, K15M, K4M and K100M. The use of a mixture of a hydroxypropylmethylcellulose having a viscosity similar to that of Methocel K100 lv, ranging between 78 and 117 mPas, and a hydroxypropylmethylcellulose having a viscosity similar to that of Methocel K4M, ranging between 2308 and 3755 mPas (again at 20° C. in 2% aqueous solution), is particularly preferred.

The compositions according to the invention will generally contain a unit dose ranging between 50 and 1200 mg of curcumin, preferably 250-500 mg of curcumin.

The weight ratio between curcumin and hydrophilic matrix ranges between 4:1 and 2:1 (preferably 3:1/2:1).

The compositions according to the invention can also contain other excipients, such as wetting agents, ionic or non-ionic surfactants, disintegrating agents, super-disintegrating agents, crosslinked polymers, complexing agents and lubricants.

Examples of said excipients include phosphatides, lecithins, sodium lauryl sulphate, sorbitan esters, sucrose palmitate, sodium lauryl sarcosinate, cholic acids, poloxamer, cyclodextrins, starches, sodium starch glycolate, croscarmellose and crosslinked polyvinylpyrrolidones.

The hydrophilic matrix of hydroxypropylmethylcellulose can optionally be modified by adding lipophilic ingredients (fatty acids, fatty alcohols, ether/ester triglycerides), water-soluble ingredients (polyols, mannitol, lactose, trehalose), water-dispersible ingredients (microcrystalline cellulose) or water-insoluble ingredients (dibasic calcium phosphate, calcium and magnesium salts) to modulate the release kinetics.

The compositions according to the invention maximise the pharmacological effect of curcumin in the treatment of irritable bowel syndrome, due to their ability to carry the active ingredient and specifically release it in the colon, and to guarantee controlled release starting from the terminal tract of the ileum and continuing through the entire colonic tract. It is also necessary to guarantee a certain homogeneity of the quantity released over time and simultaneously allow its activity at both topical and systemic level when a proportion of the active ingredient has been released. The compositions according to the invention are therefore particularly useful for the treatment of acute and chronic gastrointestinal disorders such as irritable bowel syndrome, diarrhea, constipation, Crohn's disease, ulcerating colitis, diverticulitis and inflammatory bowel disease in general.

Conventional techniques such as direct compression, wet granulation, dry compacting/granulation and melt granulation can be used to prepare the compositions according to the invention.

The product, with the addition of excipients such as wetting agents, surfactants, disintegrating agents, super-disintegrating agents, glidants, non-stick agents or lubricants is then incorporated in the hydroxypropylmethylcellulose matrix using a suitable wet or dry granulation technique, direct division, direct compression, co-grinding, melt granulation or extrusion granulation.

The outer coating, consisting of materials possessing gastroresistance and/or release properties in different intestinal pHs (pH-dependent) and/or pH-independent lag time properties (delayed-release), is then applied to the core thus obtained. According to a general embodiment of the invention, the hydroxypropylmethylcellulose matrix containing curcumin is prepared first, and various functional excipients are then added by different pharmaceutical processes to dilute the product and make it workable. The ratio of active ingredient to matrix can range between 1:1 and 1:9, and the ratio of active ingredient to excipient does not normally exceed 3:1/2:1; the optimum quantity is between 0.1% and 50%.

A variable quantity of diluents up to 50%, lubricants (0.5-3%), glidants (0.5-3%), disintegrating and super-disintegrating agents (0.1-40%) and complexing agents (0.1-40%) may be added to this mixture.

The compositions according to the invention may also contain other active ingredients with synergic, complementary or otherwise useful activities. Examples of said active ingredients include probiotics (lactobacilli, bifidobacteria), digestive enzymes (enteric juices), prebiotics (butyrates, propionates, medium-long chain fatty acids, omega-3 fatty acids or esters), fibres (psyllium, guar gum, acacia fibres, calcium polycarbophil), antispastics (trimebutine and the salts thereof, otilonium bromide and other salts, dicyclomine and the salts thereof, tiropramide, propantheline and the salts thereof, biperiden and the salts thereof, octatropine and the salts thereof, memantine and ditropan), drugs for the treatment of bowel disease (IBD) such as anti-inflammatories (mesalazine, corticosteroids, azathioprine, mercaptopurine, alpha-lipoic acid), drugs active in irritable bowel syndrome (IBS) (lubiprostone, linaclotide), extracts or active ingredients of plant origin (artichoke, astaxanthin, camomile, menthol, boswellia, green tea, echinacea), lactoferrin, and antibiotics with a local topical action such as rifaximin and rifamycin.

In terms of dissolution characteristics, contact between the compositions described above and water or enteric biological fluids generates delayed, controlled, site-specific release of the active ingredient. The excipients and polymers present in the structure regulate the wettability of the system and the homogenous dissolution of curcumin within limited release ranges, thus promoting its localised activity and continuous, gradual absorption in the gastrointestinal tract.

The following examples illustrate the invention in greater detail.

EXAMPLE 1

500 g of curcumin is loaded into a mixer/granulator with 100 g of dibasic calcium phosphate. 2 g of crospovidone, 5 g of lecithin and 200 g of hydrophilic matrix, consisting of hydroxypropylmethylcellulose (HPMC K100 lv) (100 g) and hydroxypropyl methylcellulose (HPMC K4M) (100 g), are added to the same system in sequence.

The ingredients are mixed until a homogenous dispersion of the matrices is obtained, and 10 g of magnesium stearate and 10 g of colloidal silicon dioxide are then added in sequence.

The final mixture is compressed to a unit weight of 827 mg/tablet in order to administer 500 mg of active ingredient per tablet.

The resulting tablets are then film-coated with a gastroresistant solution/suspension based on 28 g of shellac (25%), 12 g of hydroxypropylmethylcellulose and 5 g of glycerin, so that a tablet with a mean weight of 872 mg is obtained.

The tablets remain intact for at least 2 hours when subjected to a disintegration test at pH 1.2. When subjected to a dissolution test at pH 7.2 and to 2% sodium lauryl sulphate, they present the following release profile: not more than 20% after 60 minutes and not more than 40% after 480 minutes; in any event, the value must be >70% after 24 hours.

EXAMPLE 2

500 g of curcumin is loaded into a mixer/granulator with 100 g of microcrystalline cellulose. 2 g of croscarmellose, 5 g of lecithin and 200 g of hydroxypropylmethylcellulose (HPMC K100 lv) are added in sequence to the same system.

The ingredients are mixed until a homogenous dispersion of the matrices is obtained, and 10 g of magnesium stearate and 15 g of colloidal silicon dioxide are then added in sequence.

The final mixture is compressed to a unit weight of 842 mg/tablet in order to administer 500 mg of active ingredient per tablet.

The resulting tablets are then film-coated with a gastroresistant solution/suspension based on 30 g of shellac (25%), 10 g of hydroxypropyl-methylcellulose and 5 g of glycerin, so that a tablet with a mean weight of 887 mg is obtained.

The tablets remain intact for at least 2 hours when subjected to a disintegration test at pH 1.2. When subjected to a dissolution test at pH 7.2 and to 2% sodium lauryl sulphate, they present the following release profile: not more than 30% after 60 minutes, not more than 60% after 480 minutes; in any event, the value must be >80% after 24 hours.

EXAMPLE 3

500 g of curcumin is loaded into a mixer/granulator with 200 g of mannitol. 2 g of sodium starch glycolate, 5 g of lecithin and 200 g of hydrophilic matrix, consisting of hydroxypropylmethylcellulose (HPMC K 15M), are added to the same system in sequence.

The ingredients are mixed until a homogenous dispersion of the matrices is obtained, and 15 g of magnesium stearate and 10 g of colloidal silicon dioxide are then added in sequence.

The final mixture is compressed to a unit weight of 932 mg/tablet in order to administer 500 mg of active ingredient per tablet.

The resulting tablets are then film-coated with a gastroresistant solution/suspension based on 40 g of shellac (25%), 8 g of hydroxypropyl-methylcellulose and 5 g of glycerin, so that a tablet with a mean weight of 985 mg is obtained.

The tablets remain intact for at least 2 hours when subjected to a disintegration test at pH 1.2. When subjected to a dissolution test at pH 7.2 and to 2% sodium lauryl sulphate, they present the following release profile: not more than 15% after 60 minutes, not more than 65% after 480 minutes; in any event, the value must be >80% after 24 hours.

EXAMPLE 4

800 g of curcumin is loaded into a granulator/homogeniser, and 200 g of hydroxypropylmethylcellulose (HPMC K100 lv), 200 g of polyoxyethylene oxide (PEO-20NF), 480 g of mannitol and 252 g of microcrystalline cellulose are added.

The ingredients are mixed for at least 15 minutes to obtain a homogenous mixture.

3 g of croscarmellose, 25 g of lecithin, 50 g of colloidal silicon dioxide and 30 g of magnesium stearate are then added in sequence.

The final mixture is compressed to a unit weight of 510 mg/tablet in order to administer 200 mg of active ingredient per tablet.

The cores obtained are coated with an aqueous dispersion containing 80 g of ethylcellulose, 16 g of sodium alginate, 2 g of titanium dioxide and 2 g of stearic acid. A film-coating with about 25 mg of coating per tablet is obtained.

When subjected to a dissolution test, the tablets exhibit the following release profile: 0% after 120 minutes in gastric juice; not more than 25% after 60 minutes, not more than 60% after 180 minutes, and not more than 80% after 8 hours; >80% after 24 hours.

EXAMPLE 5

250 g of curcumin is loaded into a mixer/granulator with 175 g of dibasic calcium phosphate.

1 g of crospovidone and 75 g of hydrophilic matrix hydroxypropyl-methylcellulose (HPMC K15M) are added in sequence to the same system.

The ingredients are mixed until a homogenous dispersion of the matrices is obtained, and 2.5 g of magnesium stearate, 2.5 g of colloidal silicon dioxide and 4 g of glyceryl behenate are then added in sequence.

The final mixture is compressed to a unit weight of 547.5 mg/tablet in order to administer 250 mg of active ingredient per tablet.

The resulting tablets are then film-coated with a gastroresistant solution/suspension based on 80 g of shellac (25%), 10 g of hydroxypropyl-methylcellulose and 4 g of glycerin.

The tablets remain intact for at least 2 hours when subjected to a disintegration test at pH 1.2. When subjected to a dissolution test at pH 7.2 they exhibit the following release profile: not more than 30% after 60 minutes, not more than 60% after 240 minutes, and not more than 70% after 480 minutes; in any event, the value must be >70% after 24 hours.

The invention claimed is:

1. Monolithic colon-specific delayed-release pharmaceutical compositions comprising:
    a) a core with a monolithic matrix comprising hydroxypropylmethylcellulose wherein curcumin is dispersed;
    b) a gastroresistant coating of core a) selected from:
        i) coating comprising shellac, hydroxypropylmethylcellulose and glycerin, or
        ii) a coating comprising ethylcellulose, sodium alginate, titanium dioxide and stearic acid;
    wherein the core with a monolithic matrix slows the release of the active ingredient within 8-24 hours, and wherein the gastrointestinal coating provides for a lag time of at least 2-4 hours, and
    wherein the curcumin to hydroxypropylmethylcellulose weight ratio in the core ranges from 4:1 to 2:1.

2. Compositions according to claim 1 wherein the hydroxypropylmethylcellulose in core a) has an apparent viscosity at 20° C. in 2% aqueous solution ranging from 3 to 200,000 mPas.

3. Compositions according to claim 1 wherein the core comprises a mixture of two hydroxypropylmethylcelluloses having different viscosity values.

4. Compositions according to claim 3 wherein the mixture consists of one hydroxypropylmethylcellulose having an apparent viscosity ranging from 80 to 120 mPas, and one hydroxypropylmethylcellulose having a viscosity ranging from 3000 to 5600 mPas, at 20° C. in 2% aqueous solution.

5. Compositions according to claim 1 comprising 50 to 1200 mg of curcumin.

6. Compositions according to claim 1 further comprising excipients selected from wetting agents, ionic surfactants, non-ionic surfactants, water-soluble diluents, water-dispersible diluents, water-insoluble diluents, disintegrants, lubricants, glidants, and colouring agents.

7. Compositions according to claim 6 wherein said excipients are selected from phosphatides, lecithins, sodium lauryl sulphate, sorbitan esters, sucrose palmitate, sodium laurylsarcosinate, cholic acids, poloxamer, cyclodextrins, starches, sodium starch glycolate, croscarmellose, cross-linked polyvinylpyrrolidones, polyols, microcrystalline celluloses, dibasic calcium phosphate, calcium salts, and magnesium salts.

8. Compositions according to claim 1 further comprising one or more ingredients selected from probiotics, digestive enzymes, prebiotics, fibres, antispastics, anti-inflammatories, inflammatory bowel discease (IBD) active medicaments, irritable bowel syndrome (IBS) active medicaments, extracts of plant origin, active ingredients of plant origin, and antibiotics with a local topical action.

9. Method of treating inflammatory bowel disease in subjects in need thereof, said method comprising
administering to said subjects an effective amount of the compositions according to claim 1; and
thereby treating said subjects of said inflammatory bowel disease.

* * * * *